(12) United States Patent
Hsu et al.

(10) Patent No.: US 11,598,766 B2
(45) Date of Patent: Mar. 7, 2023

(54) CHEMICAL SENSOR

(71) Applicant: TAIWAN CARBON NANO TECHNOLOGY CORPORATION, Miaoli County (TW)

(72) Inventors: Ching-Tung Hsu, Miaoli County (TW); Chao-Chieh Lin, Miaoli County (TW); Yuan-Shin Huang, Miaoli County (TW); Chun-Wei Shih, Miaoli County (TW); Chia-Hung Li, Miaoli County (TW); Chun-Hsien Tsai, Miaoli County (TW); Chun-Jung Tsai, Miaoli County (TW)

(73) Assignee: TAIWAN CARBON NANO TECHNOLOGY CORPORATION, Zhunan Township, Miaoli County (TW)

(*) Notice: Subject to any disclaimer, the term of this patent is extended or adjusted under 35 U.S.C. 154(b) by 300 days.

(21) Appl. No.: 17/097,844

(22) Filed: Nov. 13, 2020

(65) Prior Publication Data
US 2021/0148897 A1  May 20, 2021

(30) Foreign Application Priority Data
Nov. 15, 2019 (TW) ................. 108141583

(51) Int. Cl.
*G01N 33/52* (2006.01)
*G01N 21/78* (2006.01)
*G01N 21/25* (2006.01)
*G01N 31/22* (2006.01)

(52) U.S. Cl.
CPC ......... *G01N 33/525* (2013.01); *G01N 21/251* (2013.01); *G01N 21/78* (2013.01); *G01N 31/22* (2013.01)

(58) Field of Classification Search
CPC .............................. G01N 33/525; G01N 21/78
See application file for complete search history.

(56) References Cited

PUBLICATIONS

Huang Xiao-wei et al., "Colorimetric sensor arrays based on chemoresponsive dyes for food odor visualization", Nov. 2018, Trends in Food Science & Technology, vol. 81, 90-107 (Year: 2018).*

* cited by examiner

*Primary Examiner* — Jennifer Wecker
*Assistant Examiner* — Mickey Huang
(74) *Attorney, Agent, or Firm* — Muncy, Geissler, Olds & Lowe, P.C.

(57) ABSTRACT

The present invention provides a chemical sensor comprising a substrate, a first colorimetric sensor array exposed and arranged in a first accommodating space of the substrate and a second colorimetric sensor array arranged in a second accommodating space of the substrate. The second accommodating space is covered with an isolating layer to isolates liquid molecules but allows gas molecules to pass through. The first colorimetric sensor array changes from a first initial color to a first indicating color according to a volatile part and a non-volatile part of an analyte, and the second colorimetric sensor array changes from a second initial color to a second indicating color according to the volatile part of the analyte, so that information of the volatile part and the non-volatile part of the analyte can be obtained simultaneously.

6 Claims, 9 Drawing Sheets

CHEMICAL SENSOR

FIELD OF THE INVENTION

The present invention relates to a chemical sensor, in particular to a chemical sensor with a colorimetric sensor array.

BACKGROUND OF THE INVENTION

Colorimetric sensor is a kind of chemical sensor, which uses the color conversion induced by chemical reaction to obtain the chemical information of the object to be detected, and the colorimetric sensor has been widely used in the fields of environmental monitoring, food monitoring and other chemical monitoring.

U.S. Patent Publication No. US20040184948A1 discloses a colorimetric sensor for detecting existence and/or concentration of an analyte. The colorimetric sensor comprises a substantially continuous reflective layer; a detection layer overlying the reflective layer, the detection layer comprising at least one polymer component, wherein an optical thickness of the detection layer is variable upon exposure to the analyte; and a semi-reflective layer overlying the detection layer having a refractive index different from a refractive index of the detection layer.

The mentioned prior art provides better color development, but there is still room for improvement.

SUMMARY OF THE INVENTION

It is a primary object of the present disclosure to address the need for improvements in conventional colorimetric sensors.

For this purpose, the present invention provides a chemical sensor which comprises a substrate, a first colorimetric sensor array and a second colorimetric sensor array. The substrate comprises a first accommodating space and a second accommodating space. The first colorimetric sensor array is exposed and arranged in the first accommodating space of the substrate. The second colorimetric sensor array is arranged in the second accommodating space of the substrate, and the second accommodating space is covered with an isolating layer which isolates liquid molecules but allows gas molecules to pass through. The first colorimetric sensor array comprises at least one first sensing material, and the second colorimetric sensor array comprises at least one second sensing material. When the substrate is placed into an analyte, the first colorimetric sensor array changes from a first initial color to a first indicating color according to a volatile part and a non-volatile part of an analyte, and the second colorimetric sensor array changes from a second initial color to a second indicating color according to the volatile part of the analyte.

Accordingly, in the first colorimetric sensor array of the present invention, the volatile part and the non-volatile part of the analyte are detected and the first indicating color can be known, and in the second colorimetric sensor array, the volatile part of the analyte is detected and the second indicating color can be known, so that the first indicating color and the second indicating color can be compared and analyzed. Information of the volatile part and information of the non-volatile part of the analyte can be obtained simultaneously.

DETAILED DESCRIPTION OF THE PREFERRED EMBODIMENTS

Figure 1:
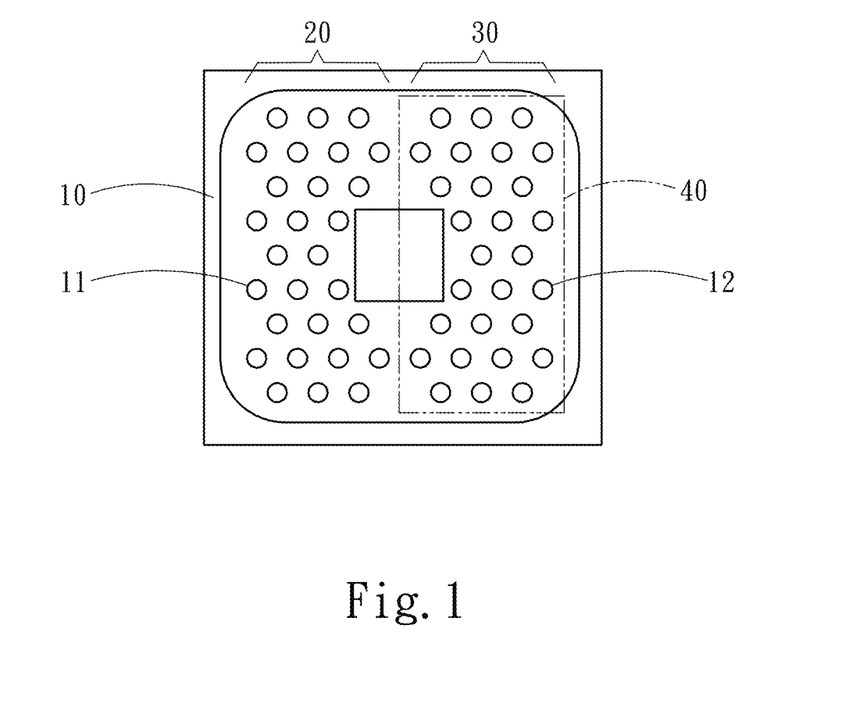
FIG. 1 is a schematic top view diagram showing the structure of an embodiment of the present invention.
Figure 2:
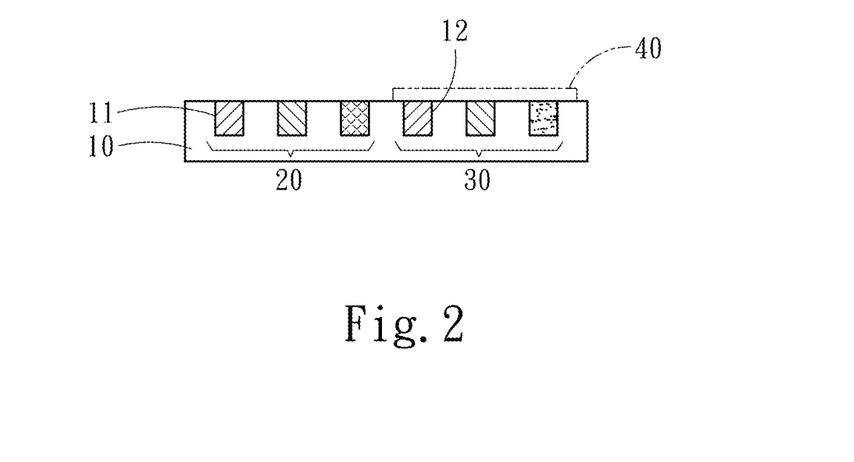
FIG. 2 is a schematic cross-sectional diagram showing the structure of an embodiment of the present invention.

With respect to the detailed description and technical aspects of the present disclosure, reference is now made to the following descriptions taken in conjunction with the accompanying drawings:

With reference to FIG. 1 and FIG. 2, the present invention provides a chemical sensor comprising a substrate 10, a first colorimetric sensor array 20 and a second colorimetric sensor array 30, wherein the substrate 10 includes a first accommodating space 11 and a second accommodating space 12, and the first colorimetric sensor array 20 is exposed and arranged in the first accommodating space 11 of the substrate 10. The second colorimetric sensor array 30 is arranged in the second accommodating space 12 of the substrate 10, and the second accommodating space 12 is covered with an isolating layer 40, the isolating layer 40 isolates liquid molecules in an analyte but allows gas molecules to pass through, and the isolating layer 40 is made of a waterproof and gas permeable material selected from porous polyurethane membrane, porous polyethylene membrane, porous polytetrafluoroethylene membrane, fibrous high-density polyethylene breathable membrane and the like. The substrate 10 may be transparent polyethylene terephthalate (PET).

The first colorimetric sensor array 20 comprises at least one first sensing material, and the second colorimetric sensor array 30 comprises at least one second sensing material, the at least one first sensing material and the at least one second sensing material respectively comprise a coloring reagent selected from a group consisting of sodium salts or mixtures of compounds of methyl red, Congo red, bromophenol blue, bromocresol purple, bromocresol green, cresol red, phenol red, thymolphthalein, resazurin, paranitrophenol, bromthymol blue, thymol blue, neutral red, crystal violet, 4-(4-nitrobenzyl) pyridine, pyrocatechol violet, chlorophenol red, nitrazine yellow, bromophenol red, m-cresol purple, Eriochrome black T, safranine, luciferin, Eosin yellow, Brilliant green, Titan yellow, Victoria blue B, carmine, litmus, curcumin, anthocyanin, alizarin red S, alizarin yellow R, indigo carmine, nile blue A, orange yellow G, Eosin B, 3,3',5,5',-tetraiodophenol sulfone phenolphthalein, bromoxylenol blue, phenol blue, disperse orange 25, acridine orange, disperse orange 3, disperse red 1, bromopyrogallol red, diaminodiphenyl acer, aminofluorescein, violet ammonium urea, 2,6-dichloroindophenol.

Also, the at least one first sensing material and the at least one second sensing material may respectively comprise a molecular barrier material selected from a group consisting of octadecanol, polyvinylpyrrolidone, polyvinyl formal, polyvinyl acetate resin, phenolic resin, epoxy resin, polybutene resin, polyethylene glycol, carbon black, carbon nanotubes, graphene, cellulose nanofibers, silicone compounds, and the like. The molecular barrier material can influence a reaction speed of the at least one first sensing material, the at least one second sensing material and target molecules to be detect, which means that the reaction speed can be regulated by selecting different materials to meet using requirement.

Figure 3A:
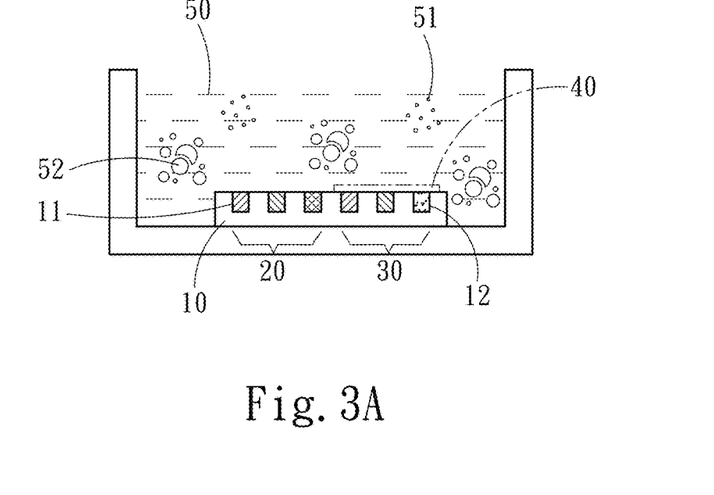
FIG. 3A is a schematic diagram I illustrating the use of an embodiment of the present invention.

With reference to FIG. 3A, the first colorimetric sensor array 20 changes from a first initial color to a first indicating color according to a volatile part 51 and a non-volatile part 52 of an analyte 50, and the second colorimetric sensor array 30 changes from a second initial color to a second indicating color according to the volatile part 51 of the analyte 50. When the substrate 10 is placed in the analyte 50, the first colorimetric sensor array 20 and the second colorimetric sensor array 30 generate the first indicating color and the second indicating color.

Figure 3B:
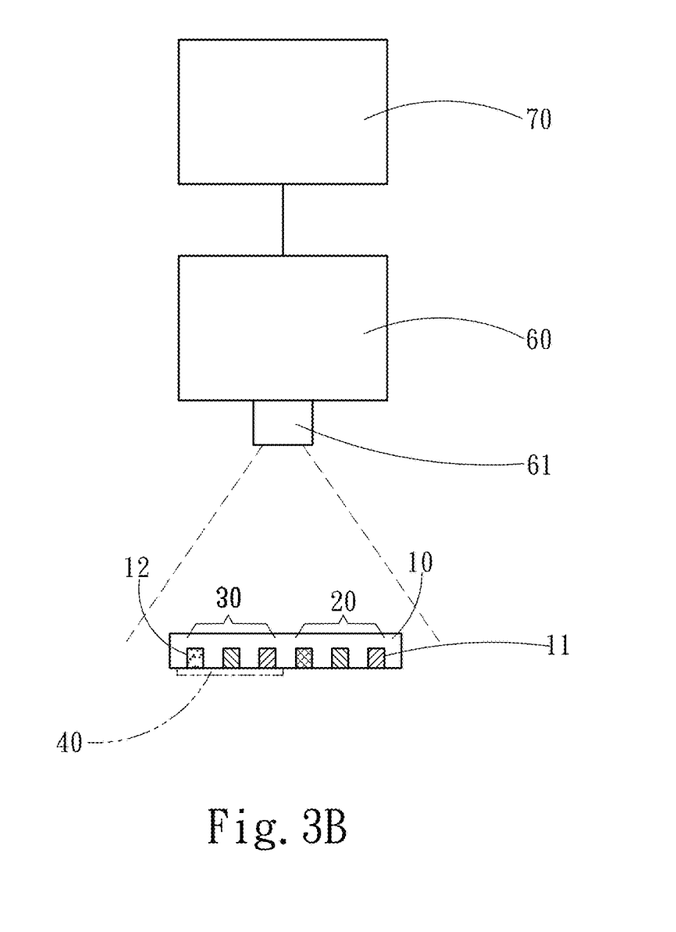
FIG. 3B is a schematic diagram II illustrating the use of an embodiment of the present invention.

With reference to FIG. 3B, the present invention further includes a hardware device 60 including an image extractor 61 that acquires an image including the first indicating color and the second indicating color, The hardware device 60 provides a component information associated with the analyte 50 according to a comparison result of the image with a predetermined database 70. That is, after the substrate 10 is taken out of the analyte 50, the image extractor 61 is aligned with the substrate 10 to obtain the first indicating color and the second indicating color, thereby obtaining the component information of the analyte 50.

Figure 4A:
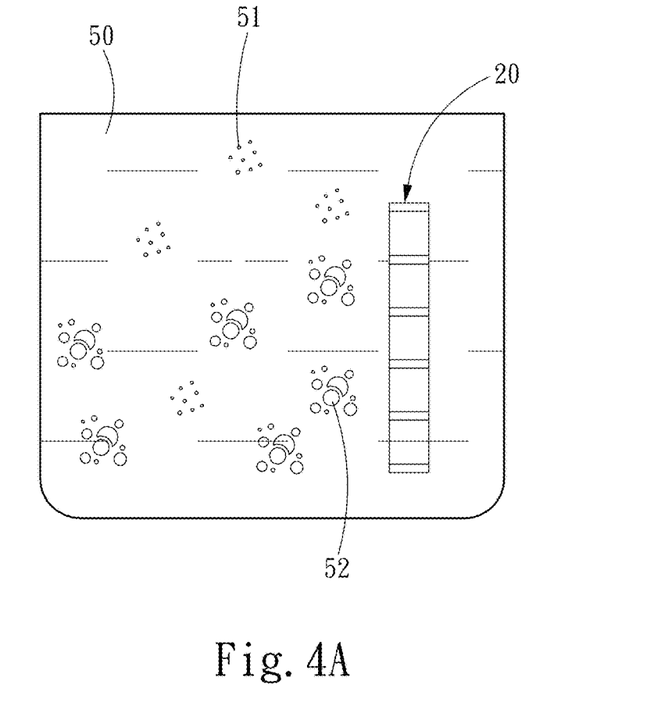
FIG. 4A is a sensing schematic diagram of a first embodiment of the present invention.
Figure 4B:
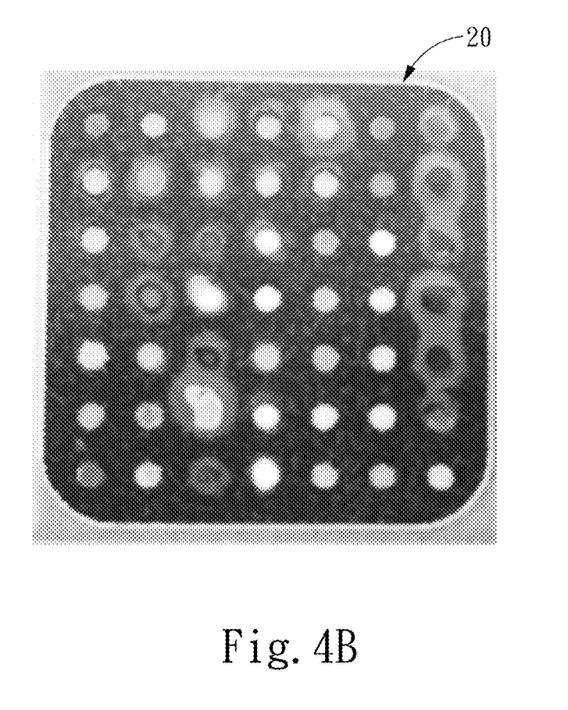
FIG. 4B is an initial photograph of the first embodiment of the present invention.
Figure 4C:
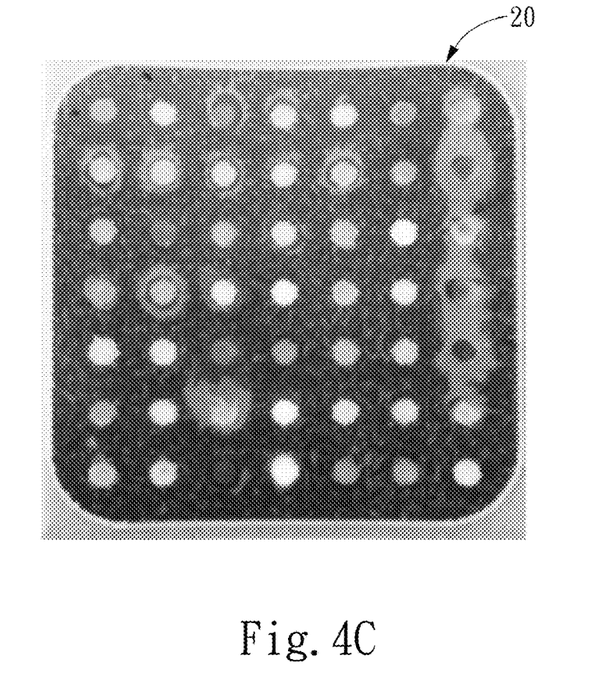
FIG. 4C is a post-reaction photograph of the first embodiment of the present invention.
Figure 5A:
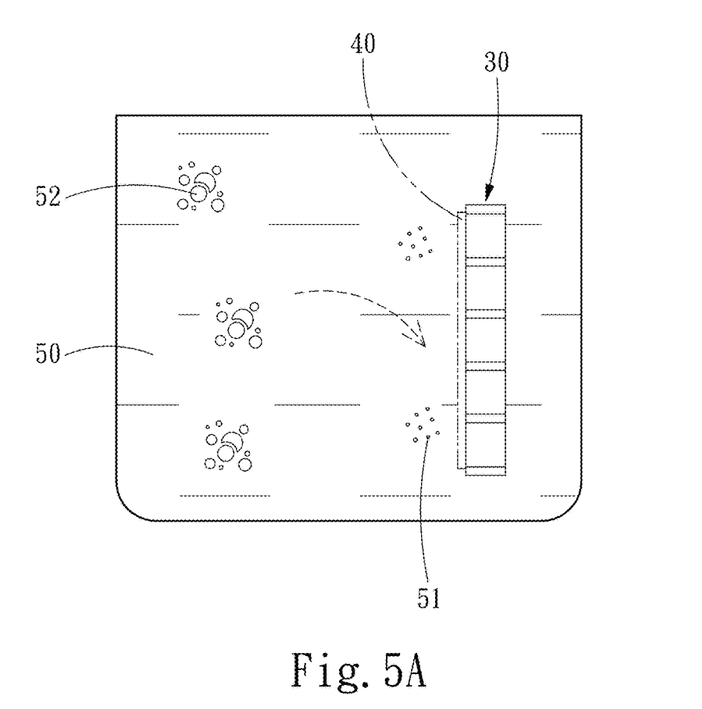
FIG. 5A is a sensing schematic diagram of a second embodiment of the present invention.
Figure 5B:
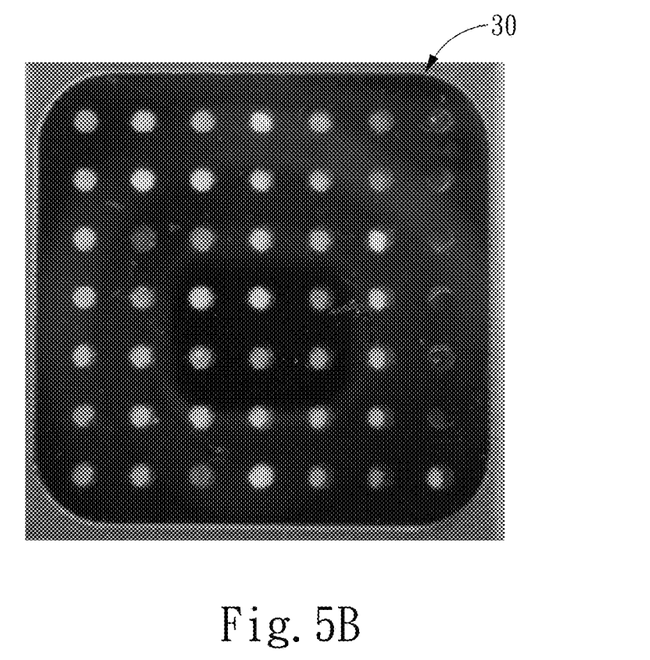
FIG. 5B is an initial photograph of the second embodiment of the present invention.
Figure 5C:
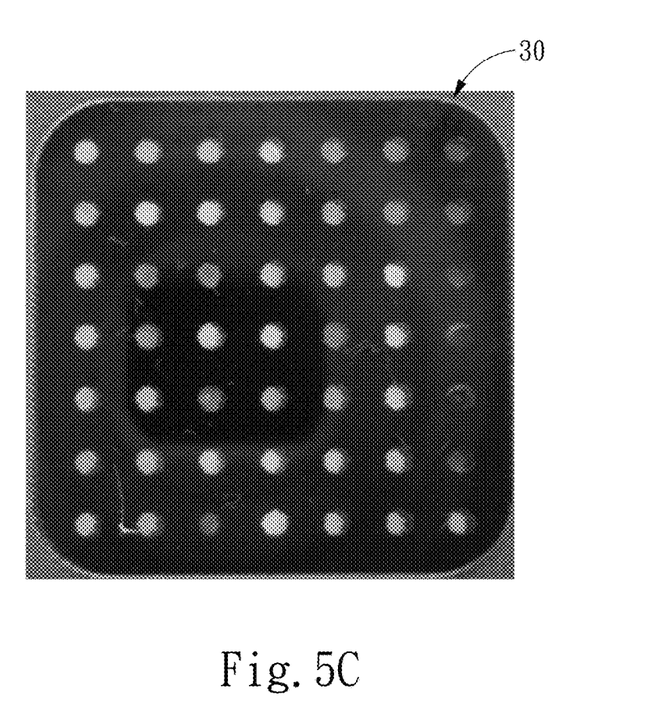
FIG. 5C is a post-reaction photograph of the second embodiment of the present invention.

Practical application of the chemical sensor of the present invention will now be exemplified and illustrated by FIG. 4A, FIG. 4B, FIG. 4C, FIG. 5A, FIG. 5B and 5C. One pill of multivitamin (Mega Multi for Men from 21ST Century HealthCare, Inc.) is dissolved in 200 g of deionized water, and insoluble matter is filtered to take a filtered solution as the analyte 50. FIG. 4A is a sensing schematic diagram that the first colorimetric sensor array 20 is placed into the analyte 50, FIG. 4B is a photograph of an initial state in which the first colorimetric sensor array 20 is not placed into the analyte 50, and FIG. 4C is a photograph that the first colorimetric sensor array 20 is placed into the analyte 50 after 8 minutes. After the first colorimetric sensor array 20 is placed in the analyte 50, the volatile part 51 and the non-volatile part 52 of the analyte 50 are absorbed by the first colorimetric sensor array 20, and then the first colorimetric sensor array 20 changes from the first initial colors to the first indicating colors, wherein the first initial colors and the first indicating colors are changing according to different coloring reagents and molecular barrier materials adopted by the first sensing material. FIG. 5A is a sensing schematic diagram that the second colorimetric sensor array 30 is placed into the analyte 50, FIG. 5B is a photograph that an initial state in which the second colorimetric sensor array 30 is not placed into the analyte 50, and FIG. 5C is a photograph that the second colorimetric sensor array 30 is placed into the analyte 50 after 19 hours. After the second colorimetric sensor array 30 is placed in the analyte 50, the isolating layer 40 isolates the analyte 50 but only allows gas molecules to pass through. Accordingly, only the volatile part 51 of the analyte 50 passes through the isolating layer 40 to be absorbed by the second colorimetric sensor array 30, and then the second colorimetric sensor array 30 changes from the second initial color to the second indicating color, wherein the second initial color and the second indicating color are changing according to different coloring agents and molecular barrier materials adopted by the second sensing material.

Figure 6A:
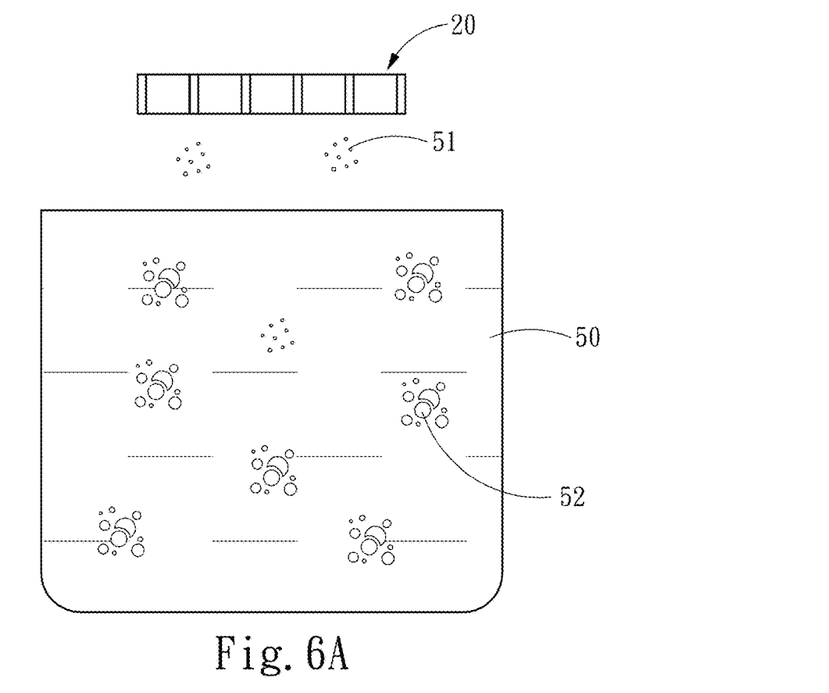
FIG. 6A is a sensing schematic diagram of a third embodiment of the present invention.
Figure 6B:
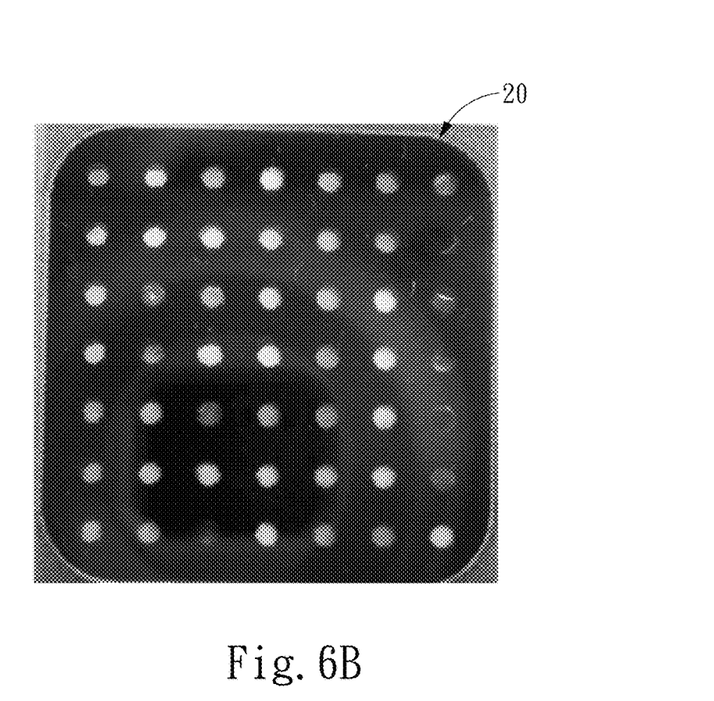
FIG. 6B is an initial photograph of the third embodiment of the present invention.
Figure 6C:
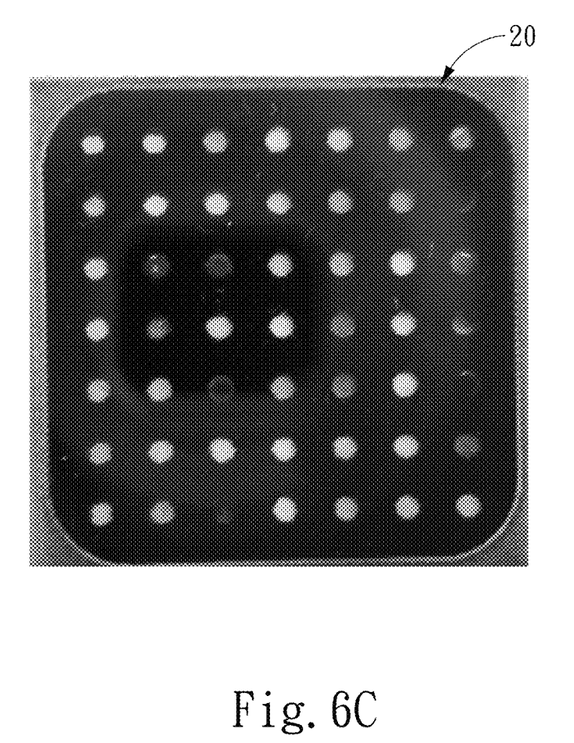
FIG. 6C is a post-reaction photograph of the third embodiment of the present invention.

With reference to FIG. 6A, FIG. 6B and 6C, the first colorimetric sensor array 20 (the second colorimetric sensor array 30 may also be used) is placed in a sensing position adjacent to the analyte 50 as shown in FIG. 6A, and FIG. 6B is a photograph that an initial state in which the first colorimetric sensor array 20 is not placed in the sensing position. FIG. 6C is a photograph that the first colorimetric sensor array 20 after being placed in the sensing position for 48 hours. Since the first colorimetric sensor array 20 is placed at the sensing position without contacting the analyte 50, thus the volatile part 51 of the analyte 50 is absorbed by the first colorimetric sensor array 20 through the air flow only, and then the first colorimetric sensor array 20 changes from the first initial color to the first indicating color, wherein the first initial color and the first indicating color are changing according to different coloring agents and molecular barrier materials adopted by the first sensing material.

Figure 7A:
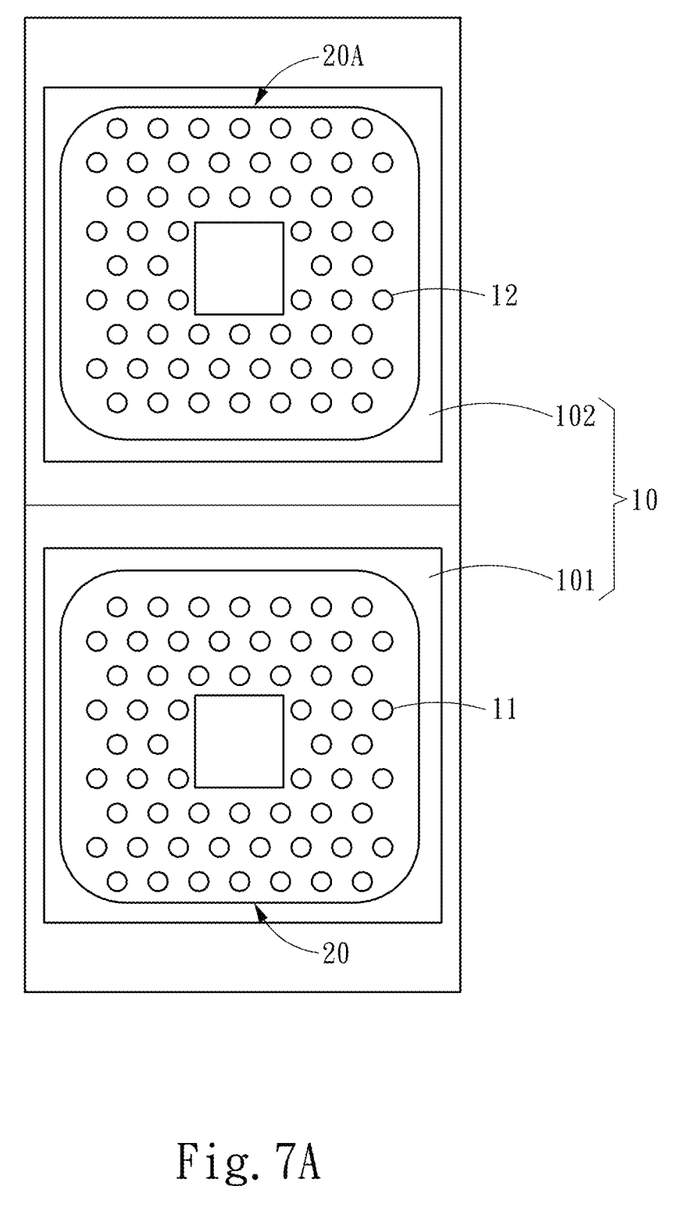
FIG. 7A is an expanded schematic diagram of a plate body of an embodiment of the present invention.
Figure 7B:
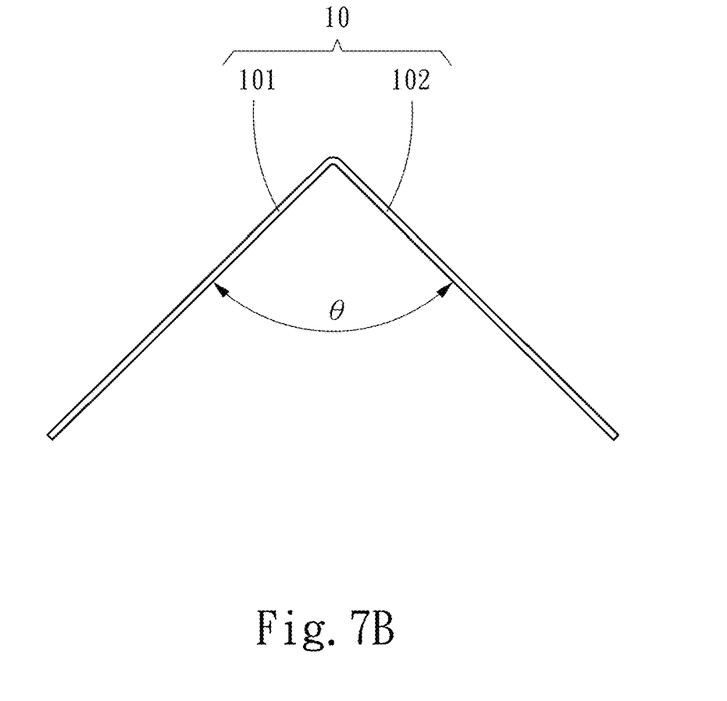
FIG. 7B is a schematic diagram showing bending of a plate body of an embodiment of the present invention.
Figure 7C:
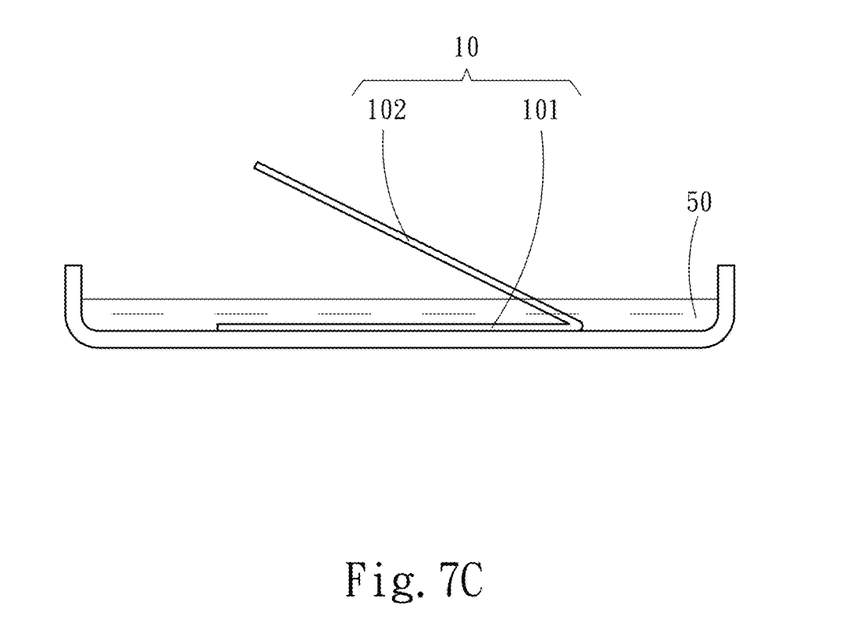
FIG. 7C is a sensing schematic diagram of an embodiment of the present invention.

With reference to FIG. 7A, FIG. 7B and FIG. 7C, in another embodiment, the substrate 10 includes a first plate body 101 and a second plate body 102, the first plate body 101 is provided with the first accommodating space 11, and the second plate body 102 is provided with the second accommodating space 12. The first plate body 101 and the second plate body 102 form an angle θ, and the angle θ can approach to 180 degrees (as shown in FIG. 7A), so that a picture can be conveniently shoot. Alternatively, the angle θ may be presented between about 40 and 80 degrees (as shown in FIG. 7B), and the first plate 101 is placed directly into the analyte 50 when the angle θ is between 40 and 80 degrees, i.e., the second plate body 102 is not placed into the analyte 50. In this embodiment, two first colorimetric sensor array 20, 20A are arranged in the first accommodating space 11 on the first plate body 101 and the second accommodating space 12 on the second plate body 102 respectively. Thus, the first colorimetric sensor array 20 is able to measure volatile part and non-volatile part of the analyte 50 to learn a first indicating color, and the first colorimetric sensor array 20A is able to measure the volatile part of the analyte 50 and knows a second indicating color. In this embodiment, the isolating layer 40 is not necessary, but may alternatively be arranged on the second accommodating space 12.

Accordingly, the characteristics of the present invention at least include:

1. The first colorimetric sensor array is exposed to and in contact with the analyte to be analogous to a human taste system (i.e., tongue), and the second colorimetric sensor array is in contact with gas molecules of the analyte but not liquid molecules of the analyte to be analogous to a human olfactory system (i.e., nose). Therefore, the chemical sensor of the present invention is able to simulate an olfactory and taste system of a human body by the arrangement of the first colorimetric sensor array and the second colorimetric sensor array.

2. The angles of the first plate body and the second plate body can be changed to meet the requirements of sensing and capturing pictures simultaneously.

What is claimed is:

1. A chemical sensor, comprising:
a substrate, comprising a first accommodating space and a second accommodating space;
a first colorimetric sensor array, exposed and arranged in the first accommodating space of the substrate and comprising at least one first sensing material; and
a second colorimetric sensor array, arranged in the second accommodating space of the substrate, the second accommodating space covered with an isolating layer which isolates liquid molecules but allows gas molecules to pass through, the second colorimetric sensor array comprising at least one second sensing material;
wherein when the substrate is placed in an analyte, the first colorimetric sensor array changes from a first initial color to a first indicating color according to a volatile part and a non-volatile part of the analyte, and the second colorimetric sensor array changes from a second initial color to a second indicating color according to the volatile part of the analyte, each of the first sensing material and the second sensing material respectively comprising a coloring agent selected from a group consisting of sodium salts or mixtures of compounds of methyl red, Congo red, bromophenol blue, bromocresol purple, bromocresol green, cresol red, phenol red, thymolphthalein, resazurin, paranitrophenol, bromthymol blue, thymol blue, neutral red, crystal violet, 4-(4-nitrobenzyl) pyridine, pyrocatechol violet, chlorophenol red, nitrazine yellow, bromophenol red, m-cresol purple, Eriochrome black T, safranine, luciferin, Eosin yellow, Brilliant green, Titan yellow, Victoria blue B, carmine, litmus, curcumin, anthocyanin, alizarin red S, alizarin yellow R, indigo carmine, nile blue A, orange yellow G, Eosin B, 3,3',5,5',-tetraiodophenol sulfone phenolphthalein, bromoxylenol blue, phenol blue, disperse orange 25, acridine orange, disperse orange 3, disperse red 1, bromopyrogallol red, diaminodiphenyl acer, aminofluorescein, violet ammonium urea, 2,6-dichloroindophenol, pyrocatechol violet.

2. The chemical sensor according to claim 1, wherein the chemical sensor further comprises a hardware device comprising an image extractor to acquire an image of one of the first indicating color and the second indicating color, the hardware device provides component information associated with the analyte according to a comparison result of the image and a predetermined database.

3. The chemical sensor according to claim 1, wherein the substrate comprises a first plate body provided with the first accommodating space and a second plate body provided with the second accommodating space, an angle is formed between the first plate body and the first plate body.

4. The chemical sensor according to claim 1, wherein the substrate is transparent polyethylene terephthalate.

5. The chemical sensor according to claim 1, wherein the first sensing material and the second sensing material respectively comprise a molecular barrier material selected from a group consisting of octadecanol, polyvinylpyrrolidone, polyvinyl formal, polyvinyl acetate resin, phenolic resin, epoxy resin, polybutene resin, polyethylene glycol, carbon black, carbon nanotubes, graphene, cellulose nanofibers, and silicone compounds.

6. The chemical sensor according to claim 1, wherein a material of the isolating layer is selected from a group consisting of a porous polyurethane membrane, a porous polyethylene membrane, a porous polytetrafluoroethylene membrane, and a fibrous high-density polyethylene gas permeable membrane.

* * * * *